United States Patent [19]

Hess et al.

[11] 4,011,262
[45] Mar. 8, 1977

[54] 13,14-DIHYDRO-15-SUBSTITUTED-ω-PENTANORPROSTAGLANDINS OF THE TWO SERIES

[75] Inventors: Hans-Jurgen E. Hess, Old Lyme; Michael R. Johnson, Gales Ferry; Jasjit S. Bindra, Groton; Thomas K. Schaaf, Old Lyme, all of Conn.

[73] Assignee: Pfizer Inc., New York, N.Y.

[22] Filed: July 3, 1974

[21] Appl. No.: 485,431

Related U.S. Application Data

[63] Continuation-in-part of Ser. Nos. 271,220, July 13, 1972, abandoned, and Ser. No. 425,519, Dec. 17, 1973, abandoned.

[52] U.S. Cl. .................. 260/520 B; 260/240 R; 260/340.5; 260/343.3 R; 260/345.7; 260/468 D; 260/373; 424/278; 424/279; 424/282; 424/308

[51] Int. Cl.$^2$ .......................................... C07C 61/06

[58] Field of Search ....... 260/520 B, 468 D, 473 R, 260/340.5

[56] References Cited

UNITED STATES PATENTS

| | | | |
|---|---|---|---|
| 3,671,570 | 6/1972 | Bagli et al. | 260/468 R |
| 3,678,092 | 7/1972 | Finch | 260/468 R |
| 3,974,213 | 8/1976 | Hess et al. | 260/520 B |

FOREIGN PATENTS OR APPLICATIONS

| | | | |
|---|---|---|---|
| 2,154,309 | 5/1972 | Germany | 260/468 D |

*Primary Examiner*—John D. Randolph
*Attorney, Agent, or Firm*—Connolly and Hutz

[57] ABSTRACT

The 15-substituted-ω-pentanorprostaglandins and various intermediates employed in their preparation. The novel prostaglandins of this invention have been found to have activity profiles comparable to the parent prostaglandins, but exhibit a greater tissue specificity of action.

13 Claims, No Drawings

13,14-DIHYDRO-15-SUBSTITUTED-ω-PENTANOR-PROSTAGLANDINS OF THE TWO SERIES

CROSS REFERENCE TO RELATED APPLICATIONS

This application is a continuation-in-part of our co-pending United States patent applications, Ser. No. 271,220 filed July 13, 1972 and now abandoned Ser. No. 425,519 filed Dec. 17, 1973 and now abandoned.

BACKGROUND OF THE INVENTION

This invention relates to certain novel analogs of the naturally occurring prostaglandins. In particular, it relates to novel 15-substituted-ω-pentanorprostaglandins and various novel intermediates useful in their preparation.

The prostaglandins are C-20 unsaturated fatty acids which exhibit diverse physiological effects. For instance, the prostaglandins of the E and A series are potent vasodilators (Bergstrom, et. al., *Acta Physiol. Scand* 64:332-33 1965 and Bergstrom, et al., *Life Sci.* 6:449-455, 1967) and lower systemic arterial blood pressure (vasodepression) on intravenous administration (Weeks and King, *Federation Proc.* 23:327, 1964; Bergstrom, et al., 1965, op. cit.; Carlson, et al., *Acta Med. Scand.* 183:423-430, 1968; and Carlson, et al., *Acta Physiol. Scand.* 75:161-169, 1969). Another well known physiological action for PGE$_1$ and PGE$_2$ is as a bronchodilator (Cuthbert, *Brit. Med. J.* 4:723-726, 1969).

Still another important physiological role for the natural prostaglandins is in connection with the reproductive cycle. PGE$_2$ is known to possess the ability to induce labor (Karim, et al., *J. Obstet. Gynaec. Brit. Cwlth.* 77:200-210, 1970), to induce therapeutic abortion (Bygdeman, et al., *Contraception*, 4, 293 (1971) and to be useful for control of fertility (Karim, *Contraception*, 3, 173 (1971)). Patents have been obtained for several prostaglandins of the E and F series as inducers of labor in mammals (Belgian Pat. No. 754,158 and West German Pat. No. 2,034,641), and on PGF$_1$, F$_2$, and F$_3$ for control of the reproductive cycle (South African Patent 69/6089). It has been shown that luteolysis can take place as a result of administration of PGF$_2\alpha$[Labhsetwar, Nature 230 528 (1971)] and hence prostaglandins have utility for fertility control by a process in which smooth muscle stimulation is not necessary.

Still other known physiological activities for PGE$_1$ are in the inhibition of gastric acid secretion (Shaw and Ramwell, In: *Worcester Symp. on Prostaglandins*, New York, Wiley, 1968, p. 55-64) and also of platelet aggregation (Emmons, et. al., *Brit. Med. J.* 2:468-472, 1967).

It is now known that such physiological effects will be produced in vivo for only a short period, following the administration of a prostaglandin. A substantial body of evidence indicates that the reason for this rapid cessation of activity is that the natural prostaglandins are quickly and efficiently metabolically deactivated by β-oxidation of the carboxylic acid side-chain and by oxidation of the 15α-hydroxyl group (Anggard, et al., *Acta. Physiol. Scand.*, 81, 396 (1971) and references cited therein). It has been shown that placing a 15-alkyl group in the prostaglandins has the effect of increasing the duration of action possibly by preventing the oxidation of the C15-hydroxyl [Yankee and Bundy, JACS 94, 3651 (1972)], Kirton and Forbes, *Prostaglandins*, 1, 319 (1972).

It was, of course, considered desirable to create analogs of the prostaglandins which would have physiological activities equivalent to the natural compounds, but in which the selectivity of action and the duration of the activity would be increased. Increased selectivity of action would be expected to alleviate the severe side effects, particularly gastrointestinal side effects, frequently observed following systemic administration of the natural prostaglandins (Lancet, 536, 1971).

SUMMARY OF THE INVENTION

These needs are met by the novel compounds of this invention, the 13,14 dihydro 15-substituted-ω-pentanorprostaglandins of the 2 series in which the substituent in question is of the structure:

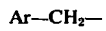

wherein Ar is α- or β-naphthyl; phenyl; 3,4-methylenedioxyphenyl; 3,4-dimethoxyphenyl; 3,4,5-trimethoxyphenyl; or monosubstituted phenyl wherein said substituent is halo, trifluoromethyl, phenyl, lower alkyl or lower alkoxyl; and in which the remaining 15-hydrogen may be replaced by a 15-lower alkyl group if desired.

Preferred embodiments of the present invention include the novel compounds of the structure:

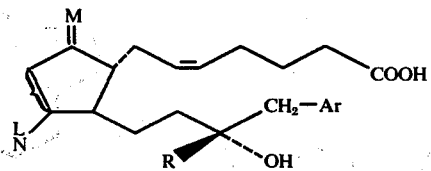

wherein Ar is α- or β-naphthyl; phenyl; 3,4-dimethoxyphenyl; 3,4-methylenedioxyphenyl; 3,4,5-trimethoxyphenyl; or monosubstituted phenyl wherein said substituent is halo, trifluoromethyl, phenyl, lower alkyl or lower alkoxy;
R is hydrogen or lower alkyl;
L is a single bond or cis double bond;
N is hydrogen or α-hydroxyl;
M is = O,

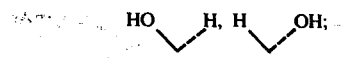

and wherein L, M and N are so selected as to complete the structure of a prostaglandin of the A, E or F series.

Preferred compounds of the present invention are those of the structure:

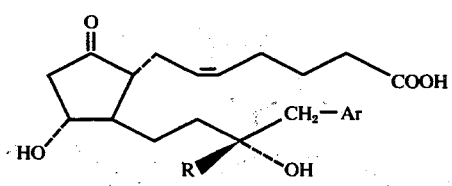

Another preferred group of compounds of the present invention are those of the structure:

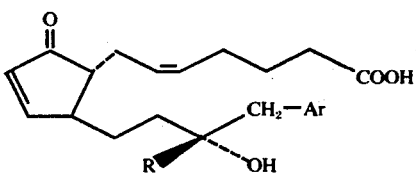

Yet another preferred group of compounds of the present invention have the structure:

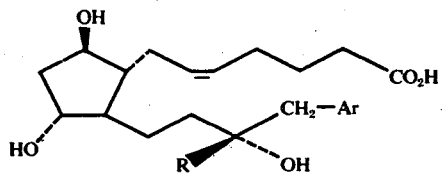

wherein Ar and R are as defined above.

In addition to the 15-substituted-ω-pentanorprostaglandins wherein the prostaglandin is 13,14-dihydro PGA$_2$, 13,14-dihydro PGF$_{2\alpha}$, 13,14-dihydro PGF$_{2\beta}$, 13,14-dihydro PGE$_2$, and 15-lower alkyl derivatives of the above compounds, this invention further comprises useful intermediates for these prostaglandins as follows:

a compound of the structure:

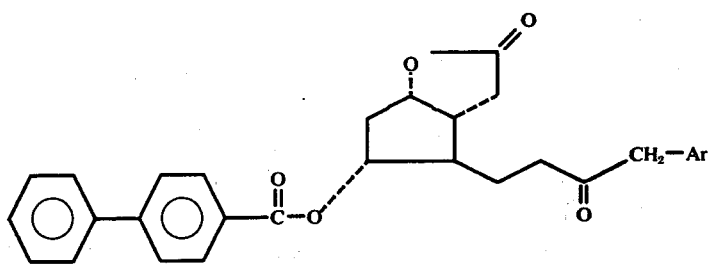

a compound of the structure:

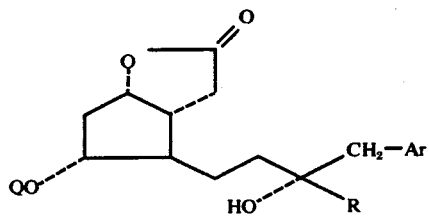

wherein R is hydrogen or lower alkyl; and Q is hydrogen or parabiphenylcarbonyl;

a compound of the structure:

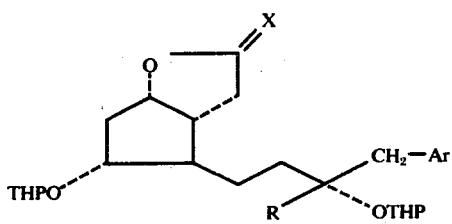

wherein THP is tetrahydropyranyl, and X is O or 

a compound of the structure:

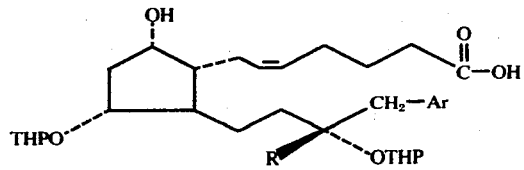

a compound of the structure:

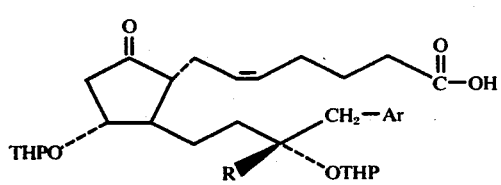

wherein THP, R and Ar are as previously defined, and especially 16-phenyl-ω-tetranor PGF$_{2\beta}$, 13,14-dihydro-16-(β-naphthyl)-ω-tetranor PGE$_2$, 16-phenyl 13,14-dihydro-15-methyl -ω-tetranor PGE$_2$, 13,14-dihydro-16-phenyl-ω-tetranor PGE$_2$, 16-phenyl 13,14-dihydro-ω-tetranor PGA$_2$, 16-β-naphthyl-ω-tetranor PGF$_{2\beta}$, 16-m-tolyl-ω-tetranor PGF$_{2\beta}$ ; 16-m-tolyl-ω-tetranor PGE$_2$; and the C$_{15}$ epimers of these compounds.

It will be understood by those skilled in the art that in structures depicting hemiacetals, no sterochemistry is implied at the lactol carbon.

It will be further understood that as herein used, the expression "prostaglandin of the 'zero' series," for example PGE$_o$, refers to prostaglandins in which the 5—6 and 13–14 double bonds have been saturated; i.e.: PGE$_o$ is 5,6, 13,14 tetrahydro PGE$_2$. In addition, the phrases "zero series", "one series" or "two series" as herein employed refer to the degree of unsaturation in the side chains, e.g., PGE$_2$, PGA$_2$, are prostaglandins of the two series whereas PGE$_1$ and PGA$_1$ are prostaglandins of the "one series". Furthermore as herein employed the phrase "lower alkyl group " refers to alkyl groups containing from 1 to 4 carbon atoms.

DETAILED DESCRIPTION OF THE INVENTION

As shown in Scheme A, the first step (1 2) is the condensation of the appropriate ester with a dialkyl methylphosphonate to produce ketophosphonate 2. Typically, the desired methyl ester is condensed with dimethyl methyl phosphonate.

In 2 3 the ketophosphonate 2 is caused to react with the known [Corey et al., J. Org. Chem. 37, 3043 (1972)] aldehyde H to produce, after chromatography or crystallization, the enone 3.

The enone 3 can be converted to a mixture of tertiary alcohols 13 and 14 by reaction with the appropriate lithium alkyl or Grignard reagent and the isomeric 13 and 14 can be separated by column or high pressure liquid chromatography. The enone 3 can be reduced with zinc borohydride to a mixture of alcohols, 4 and 5 which can be separated as above. Lithium triethyl borohydride is especially preferred when 1–2 reduction is desired. In this reaction esters such as tetrahydrofuran or 1,2 dimethoxy ethane are usually employed as solvents. Further transformations of 4 are shown on Scheme B:

4 → 6 is a base catalyzed transesterification in which the p-biphenyl-carbonyl protecting group is removed. This is most conveniently conducted with potassium carbonate in methanol or methanol-tetrahydrofuran solvent. 6 → 7 involves the protection of the two free hydroxyl groups with an acid-labile protecting group. Any sufficiently acid-labile group is satisfactory; however, the most usual one is tetrahydropyranyl, which can be incorporated in the molecule by treatment with dihydropyran and an acid catalyst in an anhydrous medium. The catalyst is usually p-toluenesulfonic acid.

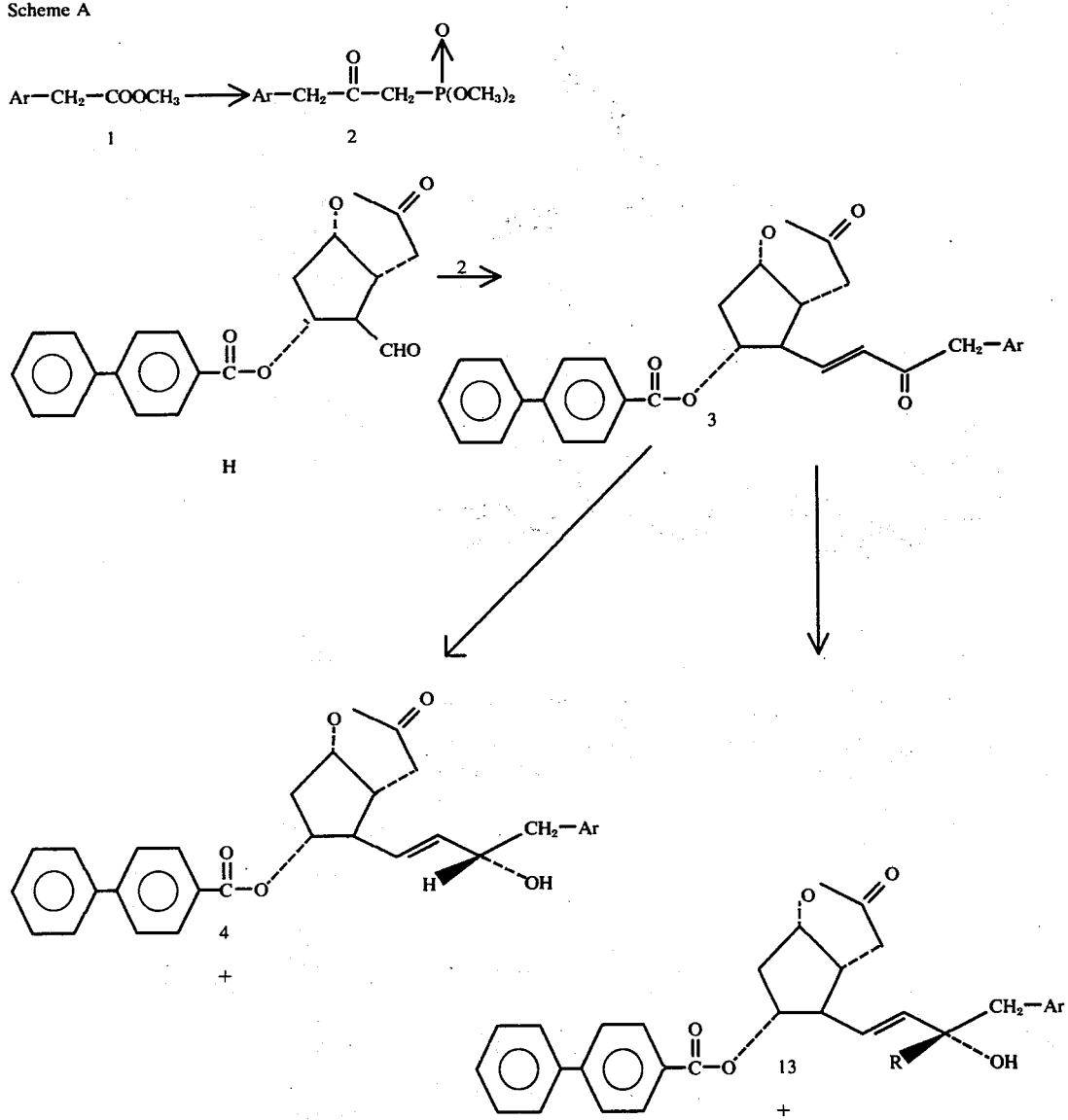

Scheme A

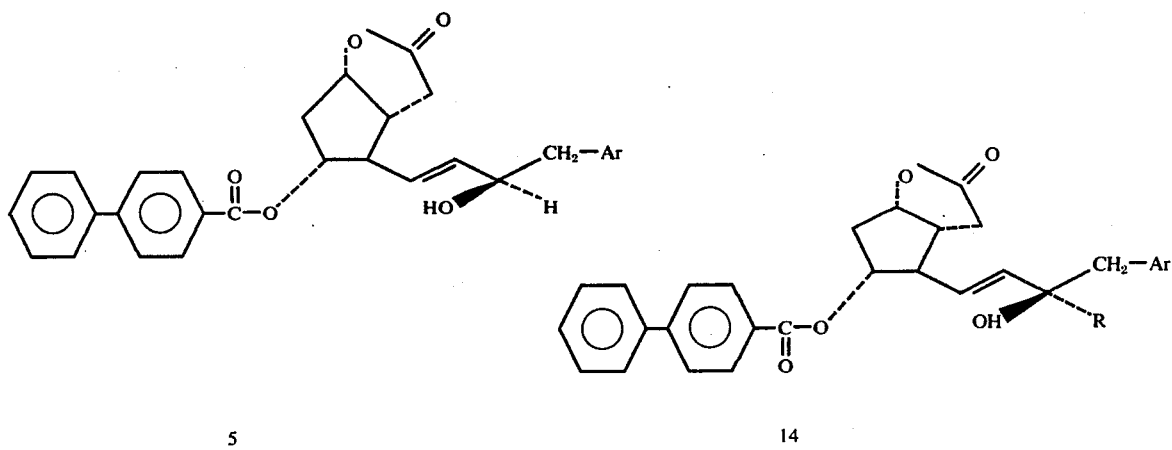
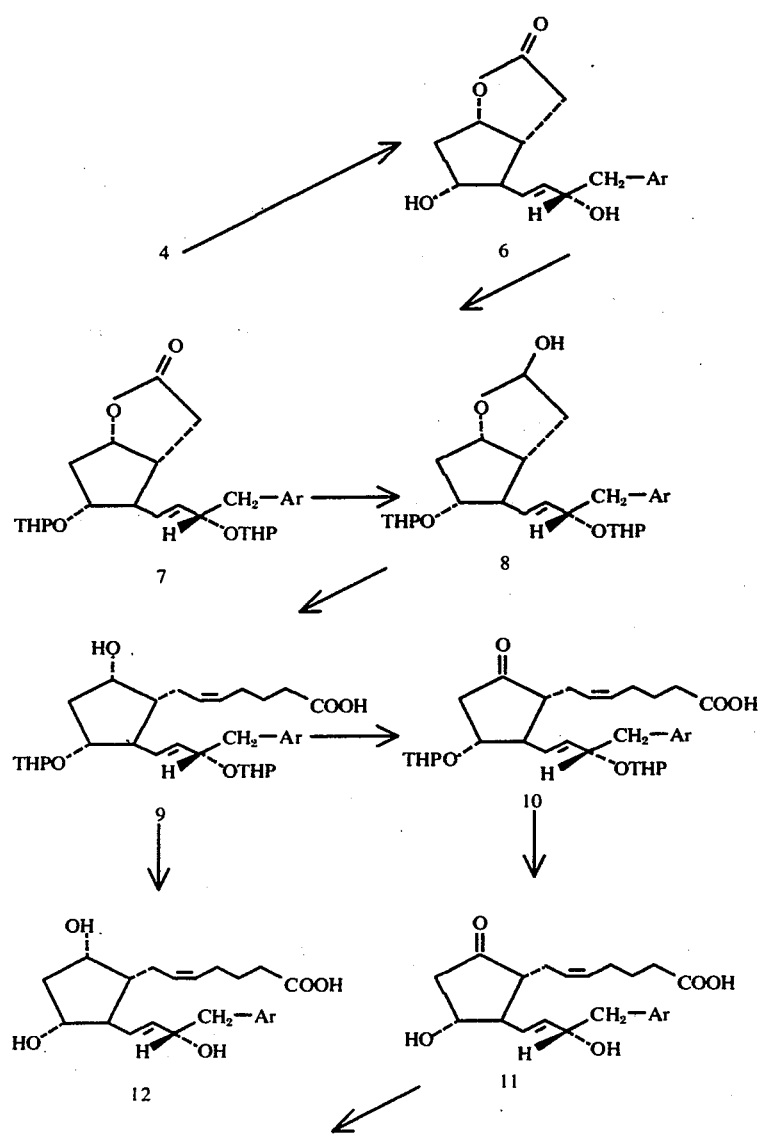
Scheme B

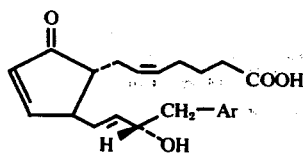

7 → 8 is a reduction of the lactone 7 to the hemiacetal 8 using diisobutyl aluminum hydride in an inert solvent. Low reaction temperatures are preferred and −60° to −70° C are usual. However, higher temperature may be employed if over-reduction does not occur. 8 is purified, if desired, by column chromatography.

8 → 9 is a Wittig condensation in which hemiacetal 8 is reacted with (4-carbohydroxy-n-butyl)triphenylphosphonium bromide in dimethyl sulfoxide, in the presence of sodium methylsulfinyl methide. 9 is purified as above.

The conversion 9 → 12 is an acidic hydrolysis of the tetrahydropyranyl groups. Any acid may be used which does not cause destruction of the molecule in the course of the removal of the protecting group; however, this is accomplished most often by use of 65 % aqueous acetic acid. The product is purified as above.

9 → 10 is an oxidation of the secondary alcohol 9 to the ketone 10. This may be accomplished using any oxidizing agent which does not attack double bonds; however, the Jones reagent is usually preferred. The product is purified as above.

10 → 11 is carried out in the same manner as 9 → 12. The product is purified as above.

11 → 15 is an acid-catalyzed dehydration. Any acid may be used for the process which does not cause extensive decomposition of the product, but the most usual procedure consists of dissolving

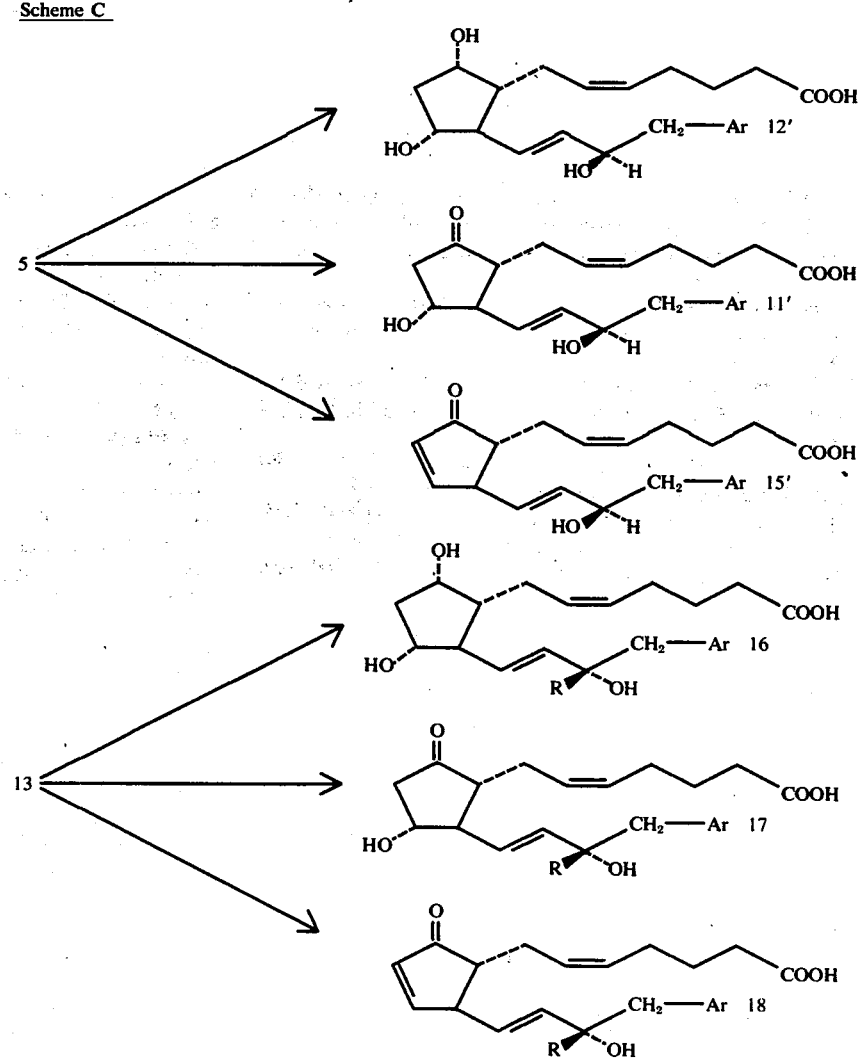

-continued

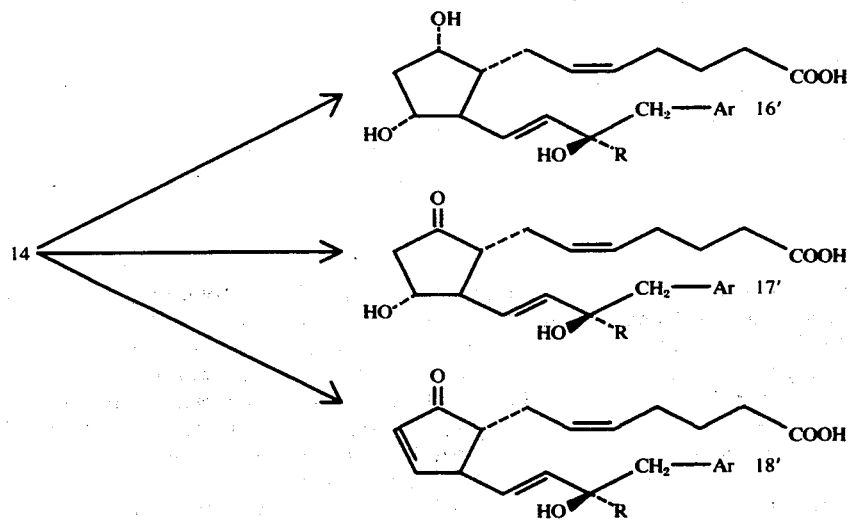

11 in an excess of 97% formic acid followed by dilution with ice water and extraction of the product after the starting material has been consumed. The product is purified as above.

As is illustrated in scheme C, 5, 13 and 14 may be substituted for 4 in scheme B to provide prostaglandin derivatives 12'–18'.

Scheme D illustrates the synthesis of precursors to the 13,14-dihydro-15-substituted-ω-pentanorprostaglandins.

In 3 → 19 + 19' the enone 3 is reduced to the tetrahydro compound through the use of any of the complex metal hydride reducing agents, $LiAlH_4$, $NaBH_4$, $KBH_4$, $LiBH_4$ and $Zn(BH_4)_2$. Especially preferred is $NaBH_4$. The products, 19 and 19', are separated from each other by column or high pressure liquid chromatography.

Furthermore, the compounds 4 and 5 Scheme A can be reduced catalytically with hydrogen to 19 and 19' respectively. The stage at which the double bond is reduced is not critical, and hydrogenation of 6 or 7 of scheme B will also afford useful intermediates for the 13,14-dihydro prostaglandin analogs of the present invention. This reduction may be achieved with either a homogenous catalyst such as tristriphenylphosphinerhodiumchloride, or with a heterogeneous catalyst such as platinum, palladium or rhodium. In a similar way the precursors to the 15-lower alkyl-15-substituted-ω-pentanorprostaglandins are synthesized by substituting compounds 13 and 14 for 4 and 5 respectively, in the synthesis Scheme D

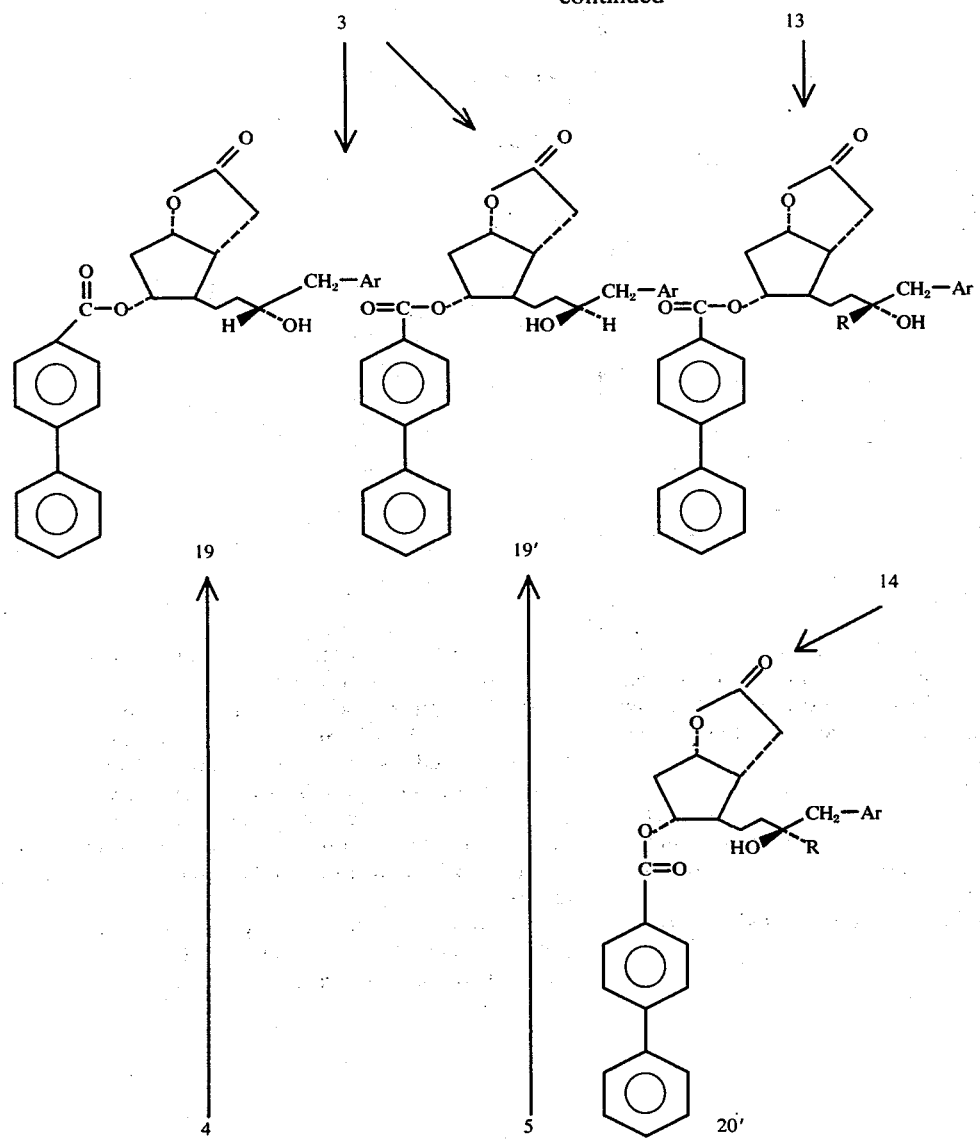

just described. The conversion of 19, 19', 20' and 20 to their respective prostaglandins follows the route shown in scheme B when 4 is replaced by 19, 19', 20' and 20 to yield the 13,14-dihydro PGE$_2$, PGA$_2$ and PGF$_2$ series of prostaglandin derivatives containing hydrogen or lower alkyl group at carbon 15.

Scheme E illustrates the preparation of the various reduced 15-substituted-ω-pentanorprostaglandin precursors:

19 → 22 is carried out as illustrated on Scheme B for 4 → 9. 22 can be used as both a precursor to a 13,14-dihydro 15-substituted-ω-pentanorprostaglandin of the 2-series or as an intermediate to 23, a precursor to a 13,14-dihydro-15-substituted-ω-pentanorprostaglandin of the 1-series. 22 → 23 is carried out by catalytic hydrogenation using the catalyst described for the reduction of 4 → 19 of Scheme D. Intermediates of the type 21 are prepared by selective reduction of the 5–6 cis double bond at low temperature using catalysts such as those described for 4 → 19 and 17 → 23. Especially preferred for this reduction is the use of palladium on carbon as a catalyst and a reaction temperature of −20°. Intermediates of the type 21 are not only precursors to 15-substituted-ω-pentanorprostaglandins of the 1-series through the route 9 → 15 of scheme B, but also as a precursor to compounds of the type 23 through the route already discussed for 22 → 23. Furthermore, the 15-substituted-ω-pentanorprostaglandins

---

Scheme E

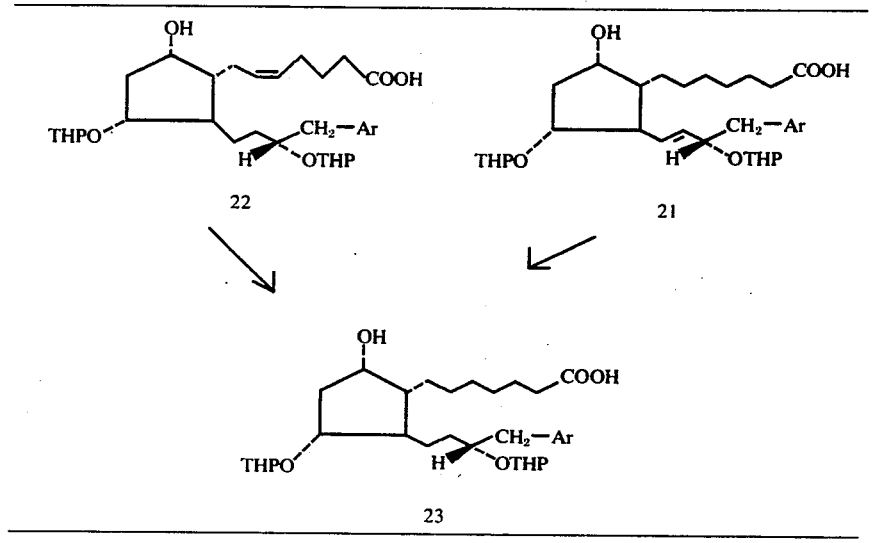

of the $E_1$ and $F_{1\alpha}$ series may be obtained directly from the corresponding prostaglandin analog of the 2-series by first protecting the hydroxyl by introducing dimethyl isopropyl silyl groups, reducing selectively the cis double bond, and removing the protecting group.

The introduction of the protecting group is usually accomplished by treatment of the prostaglandin analog with dimethyl isopropyl chlorosilane and triethylamine, the reduction is accomplished as discussed above for 9 → 21 and removal of the protecting group is accomplished by contacting the reduced protected compound with 3:1 acetic acid:water for 10 minutes or until reaction is substantially complete.

The $C_{15}$ epimers of 21, 22 and 23 can be used as precursors to the 15-epi series of prostaglandin derivatives described above, and 15-lower-alkyl-15-substituted-ω-pentanorprostaglandins reduced at the 5-6 and/or the 13,14 position and their $C_{15}$ epimers can be prepared from the appropriately substituted analogs of 9 and 19 whose syntheses follow those of Scheme A and B.

13,14-dihydro-15-lower alkyl-15-substituted-ω-pentanorprostaglandins are available from the appropriately substituted precursors via Scheme E.

Scheme F

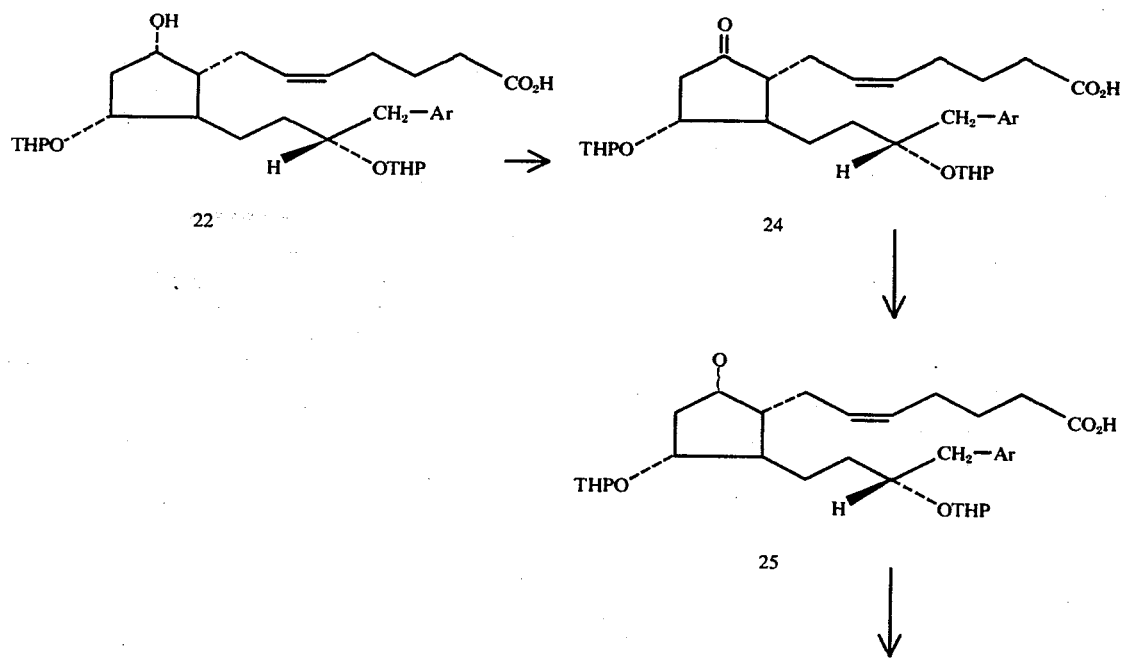

-continued

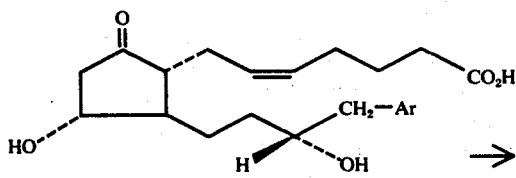

28

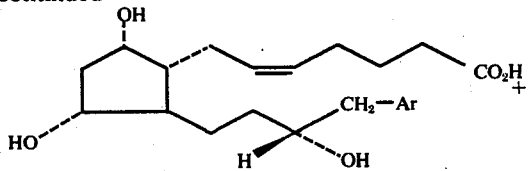

26

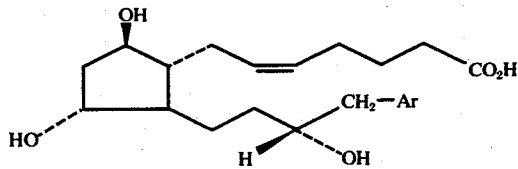

27

Scheme F illustrates the preparation of the various 13,14-dihydro 16-aryl-ω-tetranorprostaglandin $F_{2\beta}$ analogs.

22 → 24 is an oxidation of the secondary alcohol 22 to the ketone 24. This may be accomplished using any oxidizing agent which does not attack double bonds; however, the Jones reagent is usually preferred. The ketone 24 can be reduced to the epimeric alcohols 25 with a reducing agent that does not attack the carboxylic acid moiety. Sodium borohydride in ethanol or methanol or zinc borohydride in dimethoxyethane or tetrahydrofuran are usually preferred.

The conversion 25 to 26 and 27 is an acetic hydrolysis of the tetrahydropyranyl groups. Any acid may be used which does not cause destruction of the molecule in the course of the removal of the protecting groups; however, this is accomplished most often by use of 65% aqueous acetic acid. The products, 26 and 27, may be separated by column, thin layer, or high pressure liquid chromatography.

Alternatively, the ketone 28 can be reduced to 26 and 27 with a reducing agent that does not attack the carboxylic acid moiety. Sodium borohydride in ethanol or methanol or zinc borohydride in dimethoxyethane or tetrahydrofuran are usually preferred. The products, 26 and 27, may be separated by column, thin layer, or high pressure liquid chromatography.

In the foregoing procedures, where purification by chromatography is desired, appropriate chromatographic supports include neutral alumina and silica gel and 60–200 mesh silica gel is generally preferred. The chromatography is suitably conducted in reaction-inert solvents such as ether, ethyl acetate, benzene, chloroform, methylene chloride, cyclohexane and n-hexane, as further illustrated in the appended examples.

In numerous in vivo and in vitro tests we have demonstrated that the new prostaglandin analogs possess physiological activities comparable to those exhibited by the natural prostaglandins (see above). These tests include, among others, a test for effect on isolated smooth muscle from guinea pig uterus, guinea pig ileum and rat uterus, inhibition of norepinephrine-induced lipolysis in isolated rat fat cells, inhibition of histamine-induced bronchospasm in the guinea pig effect, on dog blood pressure, inhibition of stress-induced ulceration in the rat, inhibition of pentagastrin-induced hydrochloric acid excretion in rat and dog, inhibition of ADP- or collagen-induced aggregation of blood platelets, and a test for the effect on diarrhea in mice.

The physiological responses observed in these tests are useful in determining the utility of the test substance for the treatment of various natural and pathological conditions. Such determined utilities include: antihypertensive activity, bronchodilator activity, vasodilator activity, antithrombogenic activity, antiarrhythmic activity, cardiac stimulant activity, and antiulcer activity.

The novel compounds of this invention possess highly selective activity profiles compared with the corresponding naturally occuring prostaglandins and, in many cases, exhibit a longer duration of action. A prime example of the therapeutic importance of these prostaglandin analogs is the efficacy of 13,14-dihydro 16-phenyl-ω-tetranorprostaglandin $E_2$ which exhibits hypotensive activity of greatly enhanced potency and duration as compared with $PGE_2$ itself. At the same time, the smooth muscle stimulating activity is markedly depressed in comparison with $PGE_2$.

In a similar manner, other 13,14-dihydro 16-Ar-substituted $PGA_2$, $PGE_2$, $PGF_{2\alpha}$ and $PGF_{2\beta}$ exhibit desirable hypotensive activity.

In addition, the 13,14-dihydro 16-Ar-substituted prostaglandins of the E and A series are potent inhibitors of gastric acid excretion on oral administation, and as a consequence are useful for the treatment of peptic ulcers or gastric hyperacidity.

Especially useful by virtue of their selective action are the 13,14-dihydro 16-Ar-substituted-ω-pentanor-prostaglandins of the $E_2$ series. For example, 16-phenyl-13,14-dihydro-ω-tetranorprostaglandin $E_2$ is a highly selective hypotensive and gastric antiulcer agent with no significant bronchodilator activity.

The novel 15 lower alkyl compounds of this invention have the same profile of activity as the prostaglandin analogs of this invention, where R is hydrogen, from which they are derived.

All of the prostaglandins of this invention are also useful in the forms of their salts with pharmaceutically acceptable cations. Furthermore, esters at $C_9$, $C_{11}$ and $C_{15}$ in which the acyl group is lower alkanoyl, formyl, or benzoyl likewise share the utilities of the prostaglandin from which they are derived. In some cases a lower incidence of undesirable side effects accompanies the use of these esters as compared with the corresponding unesterified prostaglandins. It is obvious to one skilled in the art that these compounds include mono esters in the case of a prostaglandin of the A series, diesters in the case of prostaglandins of the E series and triesters in the case of the F series. Such esters are readily prepared by standard methods well known in the art.

The prostaglandin analogs which have a beta hydroxyl at C15 and possess a C15 lower alkyl group have action which is similar to their epimers. In some cases, however, the selectivity that these compounds display exceeds that of the epimeric compounds.

The new compounds of this invention can be used in a variety of pharmaceutical preparations which contain the compound or a pharmaceutically acceptable salt thereof, and they may be administered in the same manner as natural prostaglandins by a variety of routes, such as intravenous, oral and topical, including aerosol, intravaginal, and intranasal, among others.

The 16-Ar-substituted-ω-tetranorprostaglandins 13,14-dihydro $E_2$ and $A_2$ series are useful antiulcer agents. For the treatment of peptic ulcers these drugs are appropriately administered orally in the form of aqueous suspensions, ethanolic solutions, or preferably, in the form of capsules or tablets at doses of 0.001 to 0.10 mg/kg per dose with up to 12 doses per day.

Each of the novel compounds of the present invention are also useful in the form of their $C_1$ esters. Examples of preferred esters are those wherein the esterifying group is alkyl of from one to twelve carbon atoms; cycloalkyl of from three to eight carbon atoms; aralkyl of from seven to nine carbon atoms; phenyl or β-napthyl or mono substitutued phenyl, or β-naphthyl wherein said substituent is: halo, lower alkyl, lower alkoxyl or phenyl. Especially preferred are the p-biphenyl esters. These specific esters are valuable because they are very easily crystallized, thereby affording the opportunity to recover them in highly pure form and outstanding yield whereas prostaglandins in general ordinarily present severe crystallization problems. The new para-biphenyl esters exhibit the activities of the corresponding parent novel compounds and in addition possess the advantage of a flattened activity versus time curve which is often advantageous. They furthermore have reduced effects on gastrointestinal smooth muscle as evidenced by the reduction of side effects such as diarrhea. The new compounds in the form of the para-phenylphenol esters are prepared by procedures already described with appropriate substitution of corresponding intermediates in para-phenylphenol ester form for the intermediates employed in the foregoing reaction schemes. Thus, for example, compound 22 may be esterified with para-phenylphenol ester of a precursor to the 16-aryl, 13,14-dihydro-ω-tetranorprostaglandin para-phenylphenol esters. These can, through steps 9–11 and 11–15 be converted to the novel paraphenylphenol esters mentioned above. Further, the 13,14 dihydro-16-aryl-ω-tetranorprostaglandins of this invention can likewise be esterified with para-phenylphenol and dicyclohexylcarbodiimide to provide the desired esters.

The 16-Ar-substituted-ω-tetranorprostaglandins of the 13,14-dihydro $E_2$, $F_{2\beta}$, $F_{2\alpha}$ and $A_2$ series, are useful hypotensive agents. For treatment of hypertension these drugs could appropriately be administered as an intravenous injection at doses of about 0.5–10 μg/kg or preferably in the form of capsules or tablets at doses of 0.005 to 0.5 mg/kg/day.

To prepare any of the above dosage forms or any of the numerous other forms possible, various reaction-inert diluents, excipients or carriers may be employed. Such substances include for example, water, ethanol, gelatins, lactose, starches, magnesium stearate, talc, vegetable oils, benzyl alcohols, gums, polyalkylene glycols, petroleum jelly, cholesterol, and other known carriers for medicaments. If desired, these pharmaceutical compositions may contain auxiliary substances such as preserving agents, wetting agents, stabilizing agents, or other therapeutic agents such as antibiotics.

The following examples are merely illustrative, and in no way limit the scope of the appended claims. In these examples it will be appreciated that all temperatures are expressed in Centigrade, all melting and boiling points are uncorrected and all biological test data is expressed in terms of % activity of $PGE_2$ or administered at the same level (i.e., $PGE_2 = 100$) unless otherwise noted.

The biological data given below was obtained using the following test procedures:

Histamine-Induced Bronchoconstriction — Guinea Pigs.

Bronchodilator activities were evaluated in conscious female Reed-Willet guinea pigs (200 to 250 g) fasted overnight according to the method of Van Arman, Miller and O'Malley (1). At a pre-selected interval (pre-challenge interval) following oral or aerosol administration of water or the test drug in water, each animal was challenged with histamine aerosol as follows: a 0.4% aqueous solution of histamine was placed in a Vaponephrine Standard Nebulizer (Vaponephrine Company, Edison, New Jersey) and sprayed under an air pressure of 6 lb/in² into a closed 8 × 8 × 12 inch transparent plastic container for one min. Immediately thereafter, the guinea pig was placed in the container. The respiratory status (a reflection of bronchoconstriction) of the guinea pig after one min in the container was scored as follows: 0, normal breathing; 1, slightly deepened breathing; 2, labored breathing; 3, severely labored breathing and ataxia; 4, unconsciousness. The scores for a control group and a test group (8 animals/group) were summed and compared and the difference expressed as percent protection. (1)

1. Van Arman, C. G., Miller, L. M. and O'Malley, M. P.: SC-10,049: a catacholamine bronchodilator and hyperglycemic agent. J. Pharmacol. Exp. Ther. 133 90–97, 1961.

Dog Blood Pressure

Mongrel dogs were anesthetized with sodium pentobarbitol, 30 mg/kg/i.v. Femoral artery blood pressure was measured with a mercury manometer and recorded on smoked paper and heart rate was determined from electrocardiograms recorded from subcutaneous electrodes. Drugs were given through a cannula in a femoral vein.

Isolated Gastrointestinal and Reproductive Tissue

All measurements were made in a 2 ml tissue bath using a Phipps-Bird Linear Motion Transducer model ST-2. Tissues were allowed to respond to a stable maximum, at which point they were washed and allowed to return to baseline condition. All determinations are an average of at least three individual tissues at each reported dose. Data for analogs were compared to the dose response obtained for a natural PG in a given tissue. For purposes of potency comparisons, a standard dose of natural PG was selected; and all responses were calculated as a percentage of its response. Additional data were recorded as minimum effective dose (MED) and a consistently effective dose (CED) to establish compound detection levels for each tissue. A standard equivalent dose (SED) was determined. This value was defined as the amount of compound (ng/ml) which yielded a response that was equivalent to the tissue's response to a given dose of standard PG.

Guinea Pig Ileum: The ileum was dissected from 200–300 g male guinea pigs sacrificed by cervical dislocation. The tissue was suspended in 2 ml Tyrode solution (2) at 37° C. PGE$_2$ (30 ng/ml and/or PGF$_{2\alpha}$ (30 ng/ml) were used to establish tissue activity.

Guinea Pig Uterus (3): Nulliparous females (300–400 g) which were not in estrus were sacrificed by cervical dislocation. The dissected uteri were incubated in 2 ml of a modified Krebs solution (12) at 37° C. Uterine activity was established using PGE$_2$ (1.0 ng/ml) and/or PGF$_{2\alpha}$ (10 ng/ml).

2. Hale, L. J. ed. Biol. Lab Data. p. 92, 1958.
3. Clegg, P. C., P. Hopkinson and V. R. Pickles. J. Physiol. 167:1, 1963.
4. W. S. Umbreit, R. H. Burris and J. F. Stauffer. Monometric Techniques 148, 1957.

EXAMPLE 1

Dimethyl 2-Oxo-3-phenylpropylphosphonate (2a):

A solution of 6.2 g (50 mmoles) dimethyl methylphosphonate (Aldrich) in 125 ml dry tetrahydrofuran was cooled to −78° in a dry nitrogen atmosphere. To the stirred phosphonate solution was added 21 ml of 2.37 M n-butyllithium in hexane solution (Alfa Inorganics, Inc.) dropwise over a period of 18 minutes at such a rate that the reaction temperature never rose above −65°. After an addition 5 minutes stirring at −78°, 7.5 g (50.0 mmole) methyl phenylacetate was added dropwise at a rate that kept the reaction temperature less than −70° (20 minutes). After 3.5 hours at −78°, the reaction mixture was allowed to warm to ambient temperature, neutralized with 6 ml acetic acid and rotary evaporated (water aspirator) to a white gel. The gelatinous material was taken up in 75 ml water, the aqueous phase extracted with 100 ml portions of chloroform (3x), the combined organic extracts were backwashed (50 cc H$_2$O), dried (MgSO$_4$), and concentrated (water aspirator) to a crude residue and distilled, b.p. 134°–5° (<0.1 mm) to give 3.5 g (29%) dimethyl 2-oxo-3-phenylpropylphosphonate (2a).

The nmr spectrum (CDCl$_3$) showed a doublet centered at 3.72 δ (J=11.5 cps, 6H) for

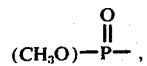

a doublet centered at 3.14δ (J=23 cps, 2H)

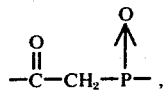

a singlet at 3.88δ (2H) for

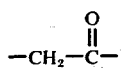

and a broad singlet at 7.22δ (5H) for C$_6$H$_5$—.

EXAMPLE 2

2-[3α-n-Phenylbenzoyloxy-5α-hydroxy-2β-(3-oxo-4-phenyl-trans-1-buten-1-yl) cyclopent-1α-yl]Acetic Acid, γ-lactone (3a):

Method A:

Dimethyl 2-oxo-3-phenylpropylphosphonate (2a) (3.4 g., 14.2 mmole) in 200 ml anhydrous ether was treated with 5.0 ml (12.5mmole) 2.5 M n-butyllithium in n-hexane (Alfa Inorganics, Inc.). in a dry nitrogen atmosphere at room temperature. After 5 min. of stirring, an additional 400 ml. of anhydrous ether was added followed by 3.85 g (11 mmole) 2-[3α-p-phenylbenzoyloxy-5α-hydroxy-2β-formylcyclopentan-1α-yl]acetic acid, γ-lactone in one portion and 50 ml anhydrous ether. After 35 minutes the reaction mixture was quenched with 5 ml glacial acetic acid, washed with 100 ml saturated sodium bicarbonate solution (4 x), 100 ml water (2 x), 100 ml saturated brine (1 x), dried (MgSO$_4$) and evaporated to yield 2.908 g (57%) 2-[3α-p-phenylbenzoyloxy-5α-hydroxy-2β-(3-oxo-4-phenyl-trans-1-buten-1-yl)cyclopent-1α-yl]acetic acid, γ-lactone (3a) as a foam after column chromatography (silica gel, Baker, 60–200 mesh), m.p. 107°–8° (ether).

Method B:

Dimethyl 2-oxo-3-phenylpropylphosphonate (2a) (2.9 g., 12mmole) in 20 ml anhydrous dimethoxyethane was treated with 4.7 ml. (11 mmole) 2.34 M n-butyllithium in n-hexane (Alfa Inorganics, Inc.) in a dry nitrogen atmosphere at room temperature. After 40 min. of stirring, 3.5 g. (10 mmole) 2-[3α-p-phenylbenzoyloxy-5α-hydroxy-2β-formylcyclopentan-1α-yl]acetic acid, γ-lactone was added in one portion followed by 15 ml anhydrous 1,2-dimethoxy ethane. After 30 minutes the reaction mixture was quenched with 1 ml glacial acetic acid, filtered, washed with 20 ml saturated sodium bicarbonate solution (2x), 20 ml saturated brine (1 x), dried (Na$_2$SO$_4$) and evaporated to yield 2 g (43%) 2-[3α-p-phenylbenzoyloxy-5α-hydroxy-2β-(3-oxo-4-phenyl-trans-1-buten-1-yl)cyclopent-1α-yl]acetic acid, γ-lactone (3a) as a solid after column chromatography (silica gel, Baker, 60–200 mesh). m.p. 107°–108° (ether).

The ir spectrum (CHCl$_3$) of the product (3a exhibited adsorption bands at 1775 cm$^{-1}$ (strong), 1715 cm$^{-1}$ (strong), 1675 cm$^{-1}$ (medium) and 1630 cm$^{-1}$ (medium) attributable to the carbonyl groups and at 973 cm$^{-1}$ for the trans double bond. The nmr spectrum (CDCl$_3$) exhibited a multiplet at 7.23-8.18δ (9H) for the p-biphenyl group, a doublet of doublets centered at 6.75 δ(1H, J = 16 cps) and a doublet centered at 6.27δ(1H, J = 16 cps) for the olefinic protons, a broad singlet at 7.20 δ (5H) for

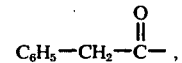

a singlet at 3.84 δ(2H) for

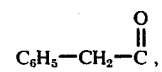

and multiplets at 4.90–5.50 δ(2H) and 2.21-3.07δ(6H) for the remainder of the protons.

EXAMPLE 3

2-[3α-p-Phenylbenzoyloxy-5α-hydroxy-2β-(3α-hydroxy-4-phenyl-trans-1-buten-1-yl)cyclopent-1α-yl]acetic acid, γ-lactone (4a) and 2-[3α-n-Phenylbenzoyloxy-5α-hydroxy-2β (3β-hydroxy-4-phenyltrans-1-buten-1-yl)cyclopent-1α-yl]acetic acid γ-lactone (5a)

To a solution of 2908 mg (6.2 mmole) 2-[3α-p-phenylbenzoyloxy-5α-hydroxy-2β-(3-oxo-4-phenyl-trans-1-buten-1-yl)cyclopent-1α-yl]acetic acid, γ-lactone (3a) in 30 ml dry 1,2-dimethoxyethane in a dry nitrogen atmosphere at ambient temperature was added dropwise 2.0 ml. of 1.0 M zinc borohydride solution in 1,2-dimethoxyethane. After stirring at 0° for 2 hours, a saturated sodium bitartrate solution was added dropwise until hydrogen evolution ceased. The reaction mixture was allowed to stir for 5 minutes at which time 250 ml dry methylene chloride was added. After drying (MgSO$_4$) and concentrating (water aspirator) the resultant semisolid was purified by column chromatography on silica gel (Baker "Analyzed" Reagent 60–200 mesh) using ether as eluent. After elution of less polar impuriites a fraction containing 658 mg 2-[3α-p-phenylbenzoyloxy-5α-hydroxy-2β-(3α-hydroxy-4-phenyl-trans-1-buten-1yl)cylcopent-1α-yl]acetic acid, γ-lactone (4a), a 480 mg fraction of mixed 4a and 5a and finally a fraction (671 mg) of 2-[3α-p-phenylbenzoyloxy-5α-hydroxy-2β-(3α-hydroxy-4-phenyl-trans-1-buten-yl)cyclopent-1α-yl]acetic acid, γ-lactone (5a).

The ir spectrum (CHCl$_3$) of 4a and 5a had strong carbonyl adsorptions at 1770 and 1715 cm$^{-1}$ and an adsorption at 970 cm$^{-1}$ for the trans double bond. The NMR spectrum (CDCl$_3$) of 4a and 5a was consistent with the assigned structure.

A product of this example (5a) may be converted to 15-epi-13,14-dihydro-16-phenyl-ω-tetranorprostaglandins of the E$_2$, A$_2$, F$_{2\alpha}$ and F$_{2\beta}$ series by the procedures of examples 10–15 and 24–27.

EXAMPLE 4

2-[3α,5α-Dihydroxy-2β-(3α-hydroxy-4-phenyl-trans-1-buten-1-yl) cyclopent-1α-yl]acetic acid, γ-lactone (6a):

A heterogeneous mixture of 658 mg (1.35 mmole) of 2-[3α-p-phenylbenzoyloxy-5α-hydroxy-2β-(3α-hydroxy-4-phenyl-trans-1-buten 1-yl)cyclopent-1α-yl]acetic acid, γ-lactone (4a), 7.1 ml. of absolute methanol and 188 mg. of finely powdered, anhydrous potassium carbonate was stirred at room temperature for one hour, then cooled to 0°. To the cooled solution was added 2.8 ml (2.8 mmole) of 1.0N aqueous hydrochloric acid. After stirring at 0° for an additional 10 minutes, 5 ml. of water was added with concomitant formation of methyl p-phenylbenzoate which was collected by filtration. The filtrate was saturated with solid sodium chloride, extracted with ethyl acetate (4 × 10 ml.), the combined organic extracts were washed with saturated sodium bicarbonate (10 ml.), dried (MgSO$_4$) and concentrated to give 381 mg of viscous, oily 2-[3α,5α-dihydroxy-2β-(3α-hydroxy-4-phenyl-trans-1-buten-1-yl)cyclopent-1α-yl]acetic acid, γ-lactone (6a).

The ir spectrum (CHCl$_3$) exhibited a strong adsorption at 1770 cm$^{-1}$ for the lactone carbonyl and medium adsorption at 965 cm$^{-1}$ for the trans-double bond.

The product of this example (6a) may be converted to 13,14-dihydro-16-phenyl-ω-tetranorprostaglandins of the E$_2$, A$_2$, F$_{2\alpha}$, and F$_{2\beta}$ series by the procedures of examples 15, 6, 10-14 and 24-27.

EXAMPLE 5

2-[3α,5α-Dihydroxy-2β-(3β-hydroxy-4-phenyl-trans-1-buten-1-yl) cyclopent-1α-yl]acetic acid, γ-lactone (6'a):

A heterogeneous mixture of 761 mg (1.57 mmole) of 2-[3α-p-phenylbenzoyloxy-5α-hydroxy-2β-(3β-hydroxy-4-phenyl-trans-1-buten-1-yl)cyclopent-1α-yl]acetic acid, γ-lactone (5a), 7.1 ml. of absolute methanol and 216 mg of finely powdered, anhydrous potassium carbonate was stirred at room temperature for one hour, then cooled to 0°. To the cooled solution was added 3.2 ml (3.2 mmole) of 1.0N aqueous hydrochloric acid. After stirring at 0° for an additional 10 minutes, 5 ml. of water was added with concomitant formation of methyl p-phenylbenzoate which was collected by filtration. The filtrate was saturated with solid sodium chloride, extracted with ethyl acetate (4 × 10 ml.), the combined organic extracts were washed with saturated sodium bicarbonate (10 ml.) dried (MgSO$_4$) and concentrated to give 382 mg (85%) of viscous, oily 2-[3α,5α-dihydroxy-2β-(3β-hydroxy-4-phenyl-trans-1-buten-1-yl) cyclopent-1α-yl]acetic acid γ-lactone (6'a).

The ir spectrum (CHCl$_3$) exhibited a strong adsorption at 1770 cm$^{-1}$ for the lactone carbonyl and medium adsorption at 965 cm$^{-1}$ for the trans-double bond.

The product of this example (6'a) may be converted to 15-epi-13,14-dihydro-16-phenyl-ω-tetranorprostaglandins of the E$_2$, A$_2$, F$_{2\alpha}$, F$_{2\beta}$ series by the procedures of examples 15, 6, 10-14 and 24-27.

EXAMPLE 6

2-[5α-Hydroxy-3α-(tetrahydropyran-2-yloxyl-2β-(3α-]tetrahydropyran-2-yloxy]-4-phenyl-trans-1-buten-1-yl)cyclopent-1α-yl]acetic acid, γ-lactone (7a).

To a solution of 38 mg (1.33 mmole) 2-[3α,5α-dihydroxy-2β-(3α-hydroxy-4-phenyl-trans-1-buten-yl)cyclopent-1α-yl]acetic acid, γ-lactone (6a) in 5 ml anhydrous methylene chloride and 0.04 ml of 2,3-dihydropyran at 0° in a dry nitrogen atmosphere was added 5 mg p-toluenesulfonic acid monohydrate. After stirring for 15 minutes, the reaction mixture was combined with 100 ml ether, the ether solution washed with saturated sodium bicarbonate (1 × 15 ml) then saturated brine (1 × 15 ml), dried MgSO$_4$) and concentrated to yield 615 mg (>100%) crude 2-[5α-hydroxy-3α-(tetrahydropyran-2-yloxy)-2β-(3β-]tetrahydropyran-2-yloxy]-4-phenyl-trans-1-buten-1yl)cyclopent-1α-yl]acetic acid, γ-lactone (7a).

EXAMPLE 7

2-[5α-Hydroxy-3α-(tetrahydropyran-2-yloxy)-2β-(3β-[tetrahydropyran-2-yloxy]-4-phenyl-trans-1-buten-1-yl)cyclopent-1α-yl]acetic acid, γ-lactone (7'a):

To a solution of 382 mg (0.71 mmole) 2-[3α,5α-dihydroxy-2β-(3β-hydroxy-4-phenyl-trans-1-buten-yl)cyclopent-1α-yl]acetic acid, γ-lactone (6'a) in 5 ml anhydrous methylene chloride and 0.4 ml of 2,3-dihydropyran at 0° in a dry nitrogen atmosphere was added 5 mg p-toluenesulfonic acid monohydrate. After stirring for 15 minutes, the reaction mixture was combined with 100 ml ether, the ether solution washed with saturated sodium bicarbonate (1 × 15 ml) then saturated brine (1 × 15 ml), dried (MgSO$_4$) and concentrated to yield 621 mg (>100%) crude 2-[5α-hydroxy-3α-(tetrahydropyran-2-yloxy)-2β-(3β-[tetrahydropyran-2-yloxy]-4-phenyl-trans-1-buten-1-yl)cyclopent-1α-yl]acetic acid, γ-lactone (7'a).

The nmr spectrum (CDCl$_3$) of 7a and 7'a exhibited a multiplet at 5.30–5.62 δ (2H) for the olefinic protons, a singlet at 7.2 δ (5H) for the phenyl protons, and multiplets at 4.36–5.18 δ (4H), 3.22–4.24 δ (9H), and 1.18–2.92 δ (16H) for the remaining protons. The ir (CHCl₃) spectrum had a medium adsorption at 970 cm⁻¹ for the trans-double bond.

The product of this example (7'a) may be converted to 15-epi-13,14-dihydro-16-phenyl-ω-tetranorprostaglandins of the A₂, E₂, F₂α or F₂β series through the procedures of examples 10–14 and 24–27.

EXAMPLE 8

2-[3α-p-Phenylbenzoyloxy-5α-hydroxy-2β-(3α-hydroxy-3β-methyl-4-phenyl-trans-1-buten-1-yl)cyclopent-1α-yl]acetic acid, γ-lactone (13a) and 2 [3α-p-Phenylbenzoyloxy-5α-hydroxy-2β (3β-hydroxy-3α-methyl-4-phenyl-trans-1-buten-1-yl)cyclopent-1α-yl]acetic acid γ-lactone (14a).

To a solution of 2908 mg (6.2 mmole) 2-[3α-p-phenyl-benzoyl oxy-5α-hydroxy-2β-(3-oxo-4-phenyl-trans-1-buten-1-yl)cyclopent-1α-yl]acetic acid, γ-lactone (3a) in 26 ml anhydrous ether and 20 ml of tetrahydrofuran (distilled from LAH) in a dry nitrogen atmosphere at −78° is added dropwise 6.8 ml of (0.92M) methyllithium in ether (Alfa). After stirring at −78° for 15 minutes the reaction is quenched by the dropwise addition of glacial acetic acid until the pH of the reaction is approximately 7. The mixture is then diluted with methylene chloride and the diluted organic solution is washed with water (1X) and with saturated brine (1X), is dried (anhydrous magnesium sulfate), and is concentrated to afford the epimeric alcohols.

The crude product is purified by chromatography to provide the 2-[3α-p-phenylbenzoyloxy-5α-hydroxy-2β-(3α-hydroxy-3β-methyl-4-phenyl-trans-1-buten-1-yl)cyclopent-1α-yl]acetic acid, γ-lactone (13a), and 2-[3α-p-phenylbenzoyloxy-5α-hydroxy-2β-(3β-hydroxy-3α-methyl-4-phenyl-trans-1-buten-yl)cyclopent-1α-yl]acetic acid, γ-lactone (14a).

The material (13a) may be converted to the 13,14-dihydro-15α-methyl-16-phenyl-ω-tetranorprostaglandins of the A₂, E₂, F₂α, and F₂β series by the procedures of Examples 15, 4, 6, 10–14, and 24–27.

This material (14a) may be converted to the 13,14-dihydro-15β-methyl-16-phenyl-ω-tetranorprostaglandins of the A₂, E₂, F₂α, and F₂β series by the procedures outlined in Examples 15, 4, 6, 10–14, and 24–27.

Other lower alkyl derivatives of the type (14a) may be prepared by substituting the appropriate alkyl lithium derivative for methyl lithium in the above procedure. These derivatives are suitable for conversion to 13,14-dihydro-15-lower alkyl-16-phenyl-ω-tetranorprostaglandins of the A₂, E₂, F₂α, and F₂β series through the sequences of Examples 15, 4, 6, 10–14, and 24–27.

EXAMPLE 9

The procedure of Example 3 in which sodium borohydride is substituted for zinc borohydride may be used to produce 19a. 19a may then be converted to 13,14-dihydro-16-phenyl-ω-tetranorprostaglandins of the A₂, E₂, F₂α or F₂β series by the procedures of Examples 4, 6, 10–14, and 24–27.

EXAMPLE 10

2-[5α-Hydroxy-3α(tetrahydropyran-2-yloxy)-2β-(3α-{tetrahydropyran-2-yloxy}-4-phenylbut-1-yl)cyclopent-1α-yl]acetic acid, γ-lactone (24a):

A stirred heterogeneous solution of 1.555 g (3.4 mmole) 2-[5α-hydroxy-3α(tetrahydropyran-2-yloxy)-2β-(3α{tetrahydropyran-2-yloxy}-4-phenyl-trans-1-buten-1-yl)cyclopent-1α-yl]acetic acid, γ-lactone (7a) and 300 mg 5% palladium on carbon in 35 ml. at absolute methanol was hydrogenated for 90 minutes. The reaction mixture was filtered through filter aid and concentrated (in vacuo) to yield 1.457 g of 2-[5α-hydroxy-3α(tetrahydropyran)-2-yloxy)-2β-(3α-{tetrahydropyran-2-yloxy}-4-phenylbut-1-yl)cyclopentan-1α-yl] acetic acid, γ-lactone (24a). The ir spectrum (CHCl₃) of 24a exhibited a lactone carbonyl adsorbtion at 1770 cm⁻¹.

EXAMPLE 11

2-[5α-Hydroxy-3α-(tetrahydropyran-2-yloxy)-2β-(3α-{tetrahydropyran-2-yloxy}-4-phenylbut-1-yl)cyclopent-1α-yl]acetaldehyde, γ-hemiacetal (25a):

A solution of 1457 mg (3.2 mmole) 2-[5α-hydroxy-3α-(tetrahydropyran-2-yloxy)-2β-(3α-{tetrahydropyran-2-yloxy}-4-phenylbut-1-yl)cyclopent-1α-yl] acetic acid, γ-lactone (24αa) in 15 ml dry toluene was cooled to −78° in a dry nitrogen atmosphere. To this cooled solution was added 5.0 ml of 20% diisobutylaluminum hydride in n-hexane (Alfa Inorganics) dropwise at such a rate so that the internal temperature never rose above −65° (3 minutes). After an additional 30 minutes of stirring at −78°, anhydrous methanol was added until gas evolution ceased and the reaction mixture was allowed to warm to room temperature. The reaction mixture was combined with 150 ml ether, washed with 50% sodium potassium tartrate solution (1 × 50 ml), dried (NA₂SO₄) concentrated, and chromatagraphed to yield 1200 mg (81.5%) 2-[5α-hydroxy-3α-(tetrahydropyran-2-yloxy)-2β-(3α-{tetrahydropyran-2-yloxy}-4-phenylbut-1-yl)cyclopent-1-yl]acetaldehyde, γ-hemiacetal (25a).

EXAMPLE 12

9α-Hydroxy-11α,15α-bis-(tetrahydropyran-2-yloxy)-16-phenyl-cis-5-ω-tetranor prostenoic acid (22a):

To a solution of 5150 mg (11.6 mmole) (4-carbohydroxy-n-butyl) triphenylphosphonium bromide in a dry nitrogen atmosphere in 10.1 ml dry dimethyl sulfoxide was added 10.8 ml (21.1 mmole) of a 1.96M solution of sodium methylsufinylmethide in dimethyl sulfoxide. To this red ylide solution was added dropwise a solution of 1200 mg (2.6 mmole) 2-[5α-hydroxy-3α-(tetrahydropyran-2-yloxy)-2β-(3α-{tetrahydropyran-2-yloxy}-4-phenyl-but-1-yl) cyclopent-1α-yl]acetaldehyde, γ-hemiacetal (25a) in 7.0 ml dry dimethyl sulfoxide over a period of 20 minutes. After an additional 2 hours stirring at room temperature, the reaction mixture was poured into ice water. The basic aqueous solution was acidified to pH∼3 with 10% aqueous hydrochloric acid. The acidic solution was extracted with ethyl acetate (3 × 100 ml) and the combined organic extracts washed once with water (50 ml.), dried (MgSO₄) and evaporated to a solid residue. This solid residue was triturated with ethyl acetate and filtered. The filtrate was purified by column chromatography on silica gel (Baker "Analyzed" Reagent 60–200 mesh) using ethyl acetate as eluent. After removal of high R_f impurities, 880 mg of 9α-hydroxy-11α,15α-bis-(tetrahydropyran-2-yloxy)-16-phenyl-cis-5-ω-tetranor prostenoic (22a) acid was collected. The ir spectrum (CHCl₃) of 22a exhibited a carbonyl adsorbtion at 1715 cm⁻¹.

The product obtained above (22a) may be converted to 16-phenyl-ω-tetranor-13,14 dihydro PGF₂α via the process of Example 14.

EXAMPLE 13

9-Oxo-11α,15α-bis-(tetrahydropyran-2-yloxy)-16-phenyl-cis-5-ω-tetranor prostenoic acid (26a):

To a solution cooled to −10° under nitrogen of 880 mg (1.68 mmole) 9α-hydroxy-11α,15α-bis-(tetrahydropyran-2-yloxy)-16-phenyl-cis-5-ω-tetranor-prostenoic acid (22a) in 15 ml. reagent grade acetone was added dropwise 0.75 ml. (2 mmole) of Jones' reagent. After 20 minutes at −10°, 0.75 ml. 2-propanol was added and the reaction mixture was allowed to stir an additional 5 minutes at which time it was combined with 100 ml. ethyl acetate, washed with water (3 × 25 ml.), dried (MgSO₄) and concentrated to give 775 mg. of 9-oxo-11α,15α-bis-(tetrahydropyran-2-yloxy)-16-phenyl-cis-5-ω-tetranor prostenoic acid (26a). The ir spectrum (CHCl₃) had carbonyl adsorbtions at 1710 and 1735 cm$^{-1}$.

EXAMPLE 14

9-Oxo-11α,15α-dihydroxy-16-phenyl-cis-5-ω-tetranor prostenoic acid (27a):

A solution of 772 mg. 9-oxo-11α,15α-bis-(tetrahydropyran-2-yloxy)-16-phenyl-cis-5-ω-tetranor-prostenoic acid (26a) in 7.0 ml. of a 65:35 mixture of glacial acetic acid:water was stirred under nitrogen at 25° for 20 hours and then was concentrated by rotary evaporation. The resultant crude oil was purified by column chromatography on silica gel (Mallinckrodt CC-4 100–200 mesh) using ethyl acetate as eluent. After elution of less polar impurities, the oily 9-oxo-11α,15α-dihydroxy-16-phenyl-cis-5-ω-tetranor prostenoic acid (27a) weighing 361 mg. was collected. The ir spectrum (CHCl₃) exhibited carbonyl bands at 1710 and 1735 cm$^{-1}$.

Biological Activity: Guinea pig uterus 1, guinea pig. histamine aerosol text 0, dog blood pressure 400 (long duration of action).

EXAMPLE 15

2-[3α-p-Phenylbenzoyloxy-5α-hydroxy-2β-(3α-hydroxy-4-phenyl-1-butylcyclopent-1α-yl]acetic acid, γ-lactone: (19a)

A solution of 14.5 g. (3.10 mmole) of 4a in 195 ml. absolute methanol containing 0.5 g. 5% palladium on carbon was hydrogenated at atmospheric pressure at room temperature for 5.5 hours. The reaction mixture was filtered through Celite and evaporated to yield 14.0 g. (95.5%) of desired 19a. The ir (CHCl₃) spectrum of 19a exhibited carbonyl adsorbtions at 1775 cm$^{-1}$ (S, lactone) and 1715 cm$^{-1}$ (S, ester) and no adsorbtion for a trans double bond.

The product obtained above (19a) may be converted into the 13,14-dihydro-16-phenyl-ω-tetranorprostaglandins of the E₂, F₂α, F₂β, and A₂ series through the procedures of Examples 4,6, 10–14, and 24–27.

EXAMPLE 16

2-[3α-p-Phenylbenzoyloxy-5α-hydroxy-2β-(3-oxo-4-phenyl-1-butylcyclopent-1α-yl]acetic acid, γ-lactone: (50a)

To a solution of 14.0 g. (30.0 mmole) 19a in 150 ml. dry acetone at 0° was added 11.9 ml. (31.0 mmole) 2.6 M Jones' reagent dropwise over a period of 7 minutes. After an additional 10 minutes 11 ml. of 2-propanol was added and the reaction mixture was combined with 1 ml. of ethyl acetate. The ethyl acetate layer was washed successively with water (3 × 100 ml.), sodium bicarbonate (1 × 100 ml.), brine (1 × 100 ml.), dried (MgSO₄) and evaporated to yield 9.5 g. of desired 50a. m.p. 84°–86°.

EXAMPLE 17

2-[3α,5α-Dihydroxy-2β-(3-oxo-4-phenyl-1-butyl)cyclopent-1α-yl]acetic acid, γ-lactone (51a)

A heterogeneous mixture of 9.5 g. (20.4 mmole) of 2-[3α-p-phenylbenzoyloxy-5α-hydroxy-2β-(3-oxo-4-phenyl-1-butyl)cyclopent-1α-yl]acetic acid, γ-lactone(50a), 100 ml. of absolute methanol 100 ml. dry THF 3.7 g. of finely powdered, anhydrous potassium carbonate was stirred at room temperature for 3.5 hours, then cooled to 0°. To the cooled solution was added 53.2 ml. (53.2 mmole) of 1.0N aqueous hydrochloric acid. After stirring at 0° for an additional 10 minutes, 50 ml. of water was added with concomitant formation of methyl p-phenylbenzoate which was collected by filtration. The filtrate was saturated with solid sodium chloride, extracted with ethyl acetate (2 × 400 ml.), the combined organic extracts were washed with saturated sodium bicarbonate (2 × 50 ml.) dried (MgSO₄) and concentrated to give 2.3 g. (39%) of viscous, oily 2-[3α,5α-dihydroxy-2β-(3-oxo-4-phenyl-1-butyl)cyclopent-1α-yl]acetic acid, γ-lactone(51a).

The ir spectrum (CHCl₃) exhibited a strong adsorption at 1770 cm$^{-1}$ for the lactone carbonyl, a strong adsorbtion at 1915 cm$^{-1}$ for the ketone carbonyl, and no adsorption at 965 cm$^{-1}$ for a trans-double bond.

EXAMPLE 18

2-[5α-Hydroxy-3α-(tetrahydropyran-2-yloxy)-2β-(3-oxo-4-phenyl-1-butyl)cyclopent-1α-yl]acetic acid, γ-lactone: (52a)

To a solution of 2.2 g. (7.65 mmole) 2-[3α,5α-dihydroxy-2β-(3-oxo-4-phenyl-1-butyl)cyclopent-1α-yl]acetic acid, γ-lactone (51a) in 35 ml. anhydrous chloroform and 0.5 ml. of 2,3-dihydropyran at 0° in a dry nitrogen atmosphere was added 5 mg. p-toluenesulfonic acid, monohydrate. After stirring for 80 minutes, the reaction mixture was combined with 350 ml. ether, the ether solution washed with saturated sodium bicarbonate (2 × 100 ml) then saturated brine (1 × 100 ml), dried (MgSO₄) and concentrated to yield 2.8 g. crude 2-[5α-hydroxy-3α-(tetrahydropyran-2-yloxy)-2β-(3-oxo-4-phenyl-1-butyl)cyclopent-1α-yl]acetic acid, γ-lactone (52a).

EXAMPLE 19

2-[5α-Hydroxy-3α(tetrahydropyran-2-yloxy)-2β-(3-hydroxy-3-methyl-4-phenyl-1-butyl)cyclopent-1α-yl]acetic acid, γ-lactone (53a)

To a solution of 2.8 g. (7.6 mmole) (52a) in 100 ml. INSTA-STARTTM (Baker) ether in a nitrogen atmosphere was added 2.8 ml. (8.4 mmole) of 3M methyl magnesium bromide dropwise over 8 minutes. After 1 hour of stirring an additional 1 ml. of methyl magnesium bromide was added. After 25 minutes the reaction was diluted with 250 ml. of ether, quenched with 25 ml. saturated ammonium chloride, dried (MgSO₄), evaporated and chromatographed (Baker, 60–200 mesh) using ether as eluent to yield 940 mg. of the desired (53a).

EXAMPLE 20

2-[5α-Hydroxy-3α-(tetrahydropyran-2-yloxy)-2β-(3-hydroxy-3-methyl-4-phenyl-1-butyl)cyclopent-1α-yl]acetaldehyde, γ-hemiacetal (54a)

A solution of 1.113 g. (2.87 mmole) 2-[5α-(tetrahydropyran-2-yloxy)-2β-(3-hydroxy-3-methyl-4-phenyl-but-1-yl)cyclopent-1α-yl]acetic acid, γ-lactone(53a) in 15 ml. dry toluene was cooled to −78° in a dry nitrogen atmosphere. To this cooled solution was added 5.0 ml. of 20% diisobutylaluminum hydride in n-hexane (Alfa Inorganics) dropwise at such a rate so that the internal temperature never rose above −65° (7 minutes). After an additional 30 minutes of stirring at −78°, anhydrous methanol was added until gas evolution ceased and the reaction mixture was allowed to warm to room temperature. The reaction mixture was combined with 150 ml. ether, washed with 50% sodium potassium tartrate solution (50 ml.), dried ($Na_2SO_4$) and concentrated to yield 798 mg. 2-[5α-hydroxy-3α-(tetrahydropyran-2-yloxy)-2β-(3-hydroxy-4-methyl-4-phenyl-but-1-yl)cyclopent-1-yl]acetaldehyde, γ-hemiacetal(54a) after column chromatography.

EXAMPLE 21

9α-Hydroxy-11α,15-bis-(tetrahydropyran-2-yloxy)-15-methyl-16-phenyl-cis-5-ω-tetranor prostenoic acid (22a):

To a solution of 3540 mg (8.0 mmole) (4-carbonhydroxy-n-butyl) triphenylphosphonium bromide in a dry nitrogen atmosphere in 10.1 ml dry dimethyl sulfoxide was added 9.2 ml (15.0 mmole) of a 1.63M solution of sodium methylsulfinylmethide in dimethyl sulfoxide. To this red ylide solution was added dropwise a solution of 798 mg (2.05 mmole) 2-[5α-hydroxy-3α-(tetrahydropyran-2-yloxy)-2β-(3-tetrahydropyran-2-yloxy-3-methyl-4-phenyl-but-1-yl)cyclopent-1α-yl]acetaldehyde, γ-hemiacetal (25a) in 5.0 ml dry dimethyl sulfoxide over a period of 7 minutes. After an additional 1 hour stirring at room temperature, the reaction mixture was poured into ice water. The basic aqueous solution was acidified to pH 3 with 10% aqueous hydrochloric acid. The acidic solution was extracted with ethyl acetate (3 × 100 ml) and the combined organic extracts washed once with water (50 ml.), dried ($MgSO_4$) and evaporated to a residue. The crude residue was purified by column chromatography on silica gel (Baker "Analyzed" Reagent 60–200 mesh) using chloroform then ethyl acetate as eluents. After removal of high $R_f$ impurities, 948 mg of 9α-hydroxy-11α,15-bis-(tetrahydropyran-2-yloxy)-15-methyl-16-phenyl-cis-5-ω-tetranor prostenoic (22a) acid was collected. The ir spectrum ($CHCl_3$) of 22a exhibited a carbonyl adsorption at 1715 $cm^{-1}$.

The product obtained above (22a) may be converted to 15-methyl-16-phenyl-ω-tetranor-13,14 dihydro $PGF_{2\alpha}$ via the process of Example 14.

EXAMPLE 22

9-Oxo-11α,15-bis-(tetrahydropyran-2-yloxy)-15-methyl-16-phenyl-cis-5-ω-tetranor prostenoic acid (26a):

To a solution cooled to −10° under nitrogen or 948 mg (2.0 mmole) 9α-hydroxy-11α,15-bis-(tetrahydropyran-2-yloxy)-15-methyl-16-phenyl-cis-5-ω-tetranorprostenoic acid (22a) in 25 ml. reagent grade acetone was added dropwise 1.0 ml. (2.67 mmole) of Jones' reagent. After 5 minutes at −10°, 1.0 ml. 2-propanol was added and the reaction mixture was allowed to stir an additional 5 minutes at which time it was combined with 150 ml. ethyl acetate, washed with water (3 × 25 ml.), dried ($MgSO_4$) and concentrated to give 810 mg. of 9-oxo-11α,15-bis-(tetrahydropyran-2-yloxy)-15-methyl-16-phenyl-cis-5-ω-tetranor prostenoic acid (26a). The ir spectrum ($CHCl_3$) had carbonyl adsorbtions at 1710 and 1735 $cm^{-1}$.

EXAMPLE 23

9-Oxo-11α,15-dihydroxy-15-methyl-16-phenyl-cis-5-ω-tetranor prostenoic acid (27a):

A solution of 810 mg. 9-oxo-11α,15-bis(tetrahydropyran-2-yloxy)-15-methyl-16-phenyl-cis-5-ω-tetranorprostenoic acid (26a) in 8.0 ml. of a 65:35 mixture of glacial acetic acid:water was stirred under nitrogen at 25° for 7 hours and then was concentrated by rotary evaporation. The resultant crude oil was purified by column chromatography on silica gel (Mallinckrodt CC-4 100–200 mesh) using chloroform then ethyl acetate as eluents. After elution of less polar impurities, the oily 9-oxo-11α,15 -dihydroxy-15-methyl-16-phenyl-cis-5-ω-tetranor prostenoic acid (27a) weighing 93 mg. was collected. The ir spectrum ($CHCl_3$) exhibited carbonyl bands at 1710 and 1735 $cm^{-1}$.

The product of this example (27a) may be converted to the 15-methyl-16-phenyl-13,14-dihydro-ω-tetranor-prostaglandins of the $A_2F_{2\alpha}$, and $F_{2\beta}$ series through the procedures of examples 24 and 25.

EXAMPLE 24

9-oxo-15α-hydroxy-16-phenyl-cis-5-cis-10-ω-tetranorprostadienoic acid (28a)

A solution of 94 mg of 9-oxo-11α,15α-dihydroxy-16-phenyl-cis-5-ω-tetranorprostenoic acid in 5 ml of acetic acid was heated at 70° under nitrogen for 18 hours. The solution was then let cool and was azeotroped under reduced pressure with benzene (2x). The crude product was purified by silica gel chromatography (Mallinckrodt CC-7) using mixtures of benzene: chloroform as eluents to provide the desired 9-oxo-15α-hydroxy-16-phenyl-cis-5-cis-10-ω-tetranorprostadienoic acid as a colorless oil weighing 24 mg.

EXAMPLE 25

9α-11α,15α-Trihydroxy-16-phenyl-cis-5-ω-tetranorprostenoic acid (29A) and 9β,11α,15α-trihydroxy-16-phenyl-cis-5-ω-tretanorprostenoic acid (30a):

To a solution of 500 mg (1.34 mmole) of 9-oxo-11α,15α-dihydroxy-16-phenyl-cis-5-ω-tetranorprostenoid acid in 70 ml of methanol, cooled to 0°, was added to a cooled solution of 2 g of sodium borohydride in 250 ml of methanol. The solution was stirred at 0° under nitrogen for 45 minutes then was concentrated. The residue was dissolved in ethyl acetate then 10% hydrochloric acid was added until acidic. The aqueous layer was extracted with ethyl acetate (3x) and the combined organic extracts were washed with water and saturated brine, were dried (anhydrous magnesium sulfate), and were concentrated. Purification of the crude residue by silica gel chromatography (Mallinckrodt CC-7) using mixtures of methanol in methylene chloride as eluents provided first the 9α,11α,15α-trihydroxy-16-phenyl-cis-5-ω-tetranorprostenoic acid as a colorless oil weighing 152 mg then the 9β,11α,15α-trihydroxy-16-phenyl-cis-5-ω-tetranorprostenoic acid as a colorless oil weighing 210 mg.

EXAMPLE 26

9-Hydroxy-11α,15α-bis-(tetrahydropyran-2-yloxy)-16-phenyl-cis-5-ω-tetranorprostenoic acid (31a):

To a solution of 948 mg (20 mmoles) of 9-oxo-11α,15α-bis-(tetrahydropyran-2-yloxy)-16-phenyl-cis-5-ω- tetranorprostenoic acid in 70 ml of methanol, cooled to 0°, is added a cooled solution of 2.0 g of sodium borohydride in 250 ml of methanol. The solution is stirred at 0° under nitrogen for 1 hour, then is concentrated. The residue is dissolved in ethyl acetate then 10% hydrochloric acid is added until acidic. The aqueous layer is extracted with ethyl acetate and the combined organic extracts are washed with water and saturated brine, are dried (anhydrous magnesium sulfate), and are concentrated to afford the desired crude 9-hydroxy-11α,15α-bis-(tetrahydropyran-2-yloxy)-16-phenyl-cis-5-ω-tetranorprostenoic acid.

EXAMPLE 27

9α,11α,15α-Trihydroxy-16-phenyl-cis-5-ω-tetranorprostenoic acid (29a) and 9β,11α,15α-trihydroxy-16-phenyl-cis-5-ω-tetranorprostenoic acid (30a):

A solution of 900 mg of 9-hydroxy-11α,15α,-bis-(tetrahydropyran-2-yloxy)-16-phenyl-cis-5-ω-tetranorprostenoic acid in 9 ml of a 63:35 mixture of acetic acid:water is stirred at room temperature for 20 hours under nitrogen then is concentrated. Purification of the crude residue by silica gel chromatography provides the desired 9α,11α,15α-trihydroxy-16-phenyl-cis-5-ω-tetranorprostenoic acid and the 9β,11α,15α-trihydroxy-16-phenyl-cis-5-ω-tetranorprostenoic acid.

Concentration (in vacuo) and column chromatography of silica gel (Baker, 60–200 mesh) yielded 26 mg. of the β-naphthyl ester of 16-phenyl-13,14-dihydro-ω-tetranorprostaglandin E₂, m.p. 76°–9°, after crystallization from ether-pentane. The mas spectrum exhibited a characteristic peak at 482 (M-H₂O). The ir (KBr) had carbonyl adsorptions at 5.65μ and 5.75μ.

Additional compounds of the structure (a)

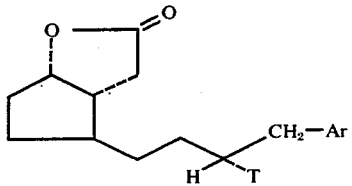

| Ar | T | IR Data |
|---|---|---|
| β-naphthyl | -OTHP | 1770 |
| β-naphthyl | -OTHP | 1770 |
| phenyl | -OTHP | 1770 |
| phenyl | -OTHP | 1770 |
| 3,4-dimethoxyphenyl | -OTHP | 1770 |
| 3,4-dimethoxyphenyl | -OTHP | 1770 |

(a) prepared by the procedure of example 6.

Additional compounds of the structure

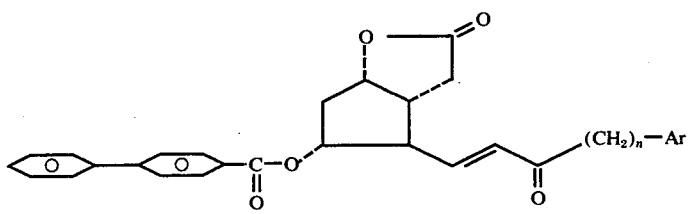

| Ar | n | m.p. | No. (a) | IR Data |
|---|---|---|---|---|
| -naphthyl | 1 | 120–128 | 2 | 1710, 1770, 1625, 1670, 970 |
| 3,4-dimethoxyphenyl | 1 |  | 2 | 1715, 1770, 1625, 1670, 970 |

(a) prepared by the procedure of the cited example

EXAMPLE 28

β-Naphthyl Ester of 16-phenyl-13,14-dihydro-ω-tetranorprostaglandins E₂:

A solution of 50 mg. (0.133 mmole) 16-phenyl-13,14-dihydrotetranorprostaglandin E₂, 216 mg. (1.5 mmole) β-naphthyl 1.9 ml. of 0.1 M dicyclohexylcarbodiimide in methylene chloride and 7 ml. methylene chloride was stirred overnight at room temperature.

(Additional Compounds)

$$Ar-(CH_2)_n-\overset{O}{\underset{\|}{C}}-CH_2-\overset{O}{\underset{\|}{P}}(OCH_3)_2$$

| Ar | n | b.p./m.p.C° | No. (a) | NMR data (Jcps) |
|---|---|---|---|---|
| -naphthyl | 1 | 195–200° ( 1mm) | 1 | 3.72 (11.5)*, 3.09 (22)** |
| 3,4-dimethoxyphenyl | 1 | (b) | 1 | 3.77 (11.5)*, 3.11 (23)** |
| m-tolyl | 1 | 158–162 (0.4 mm) | 1 | 3.6 (11)*, 3.13 (22.5)** |

(a) compound prepared by the procedure of example cited.
(b) purified by column chromatography
* methoxyl protons
** 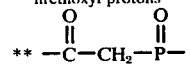

Additonal Compounds of the structure (a)

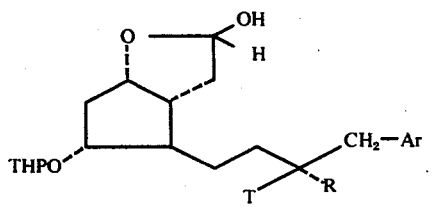

| Ar | T | R |
|---|---|---|
| β-naphthyl | α-OTHP | H |
| β-naphthyl | β-OTHP | H |
| phenyl | α-OTHP | H |
| phenyl | -OH | CH₃ |
| phenyl | β-OTHP | H |
| 3,4-dimethoxyphenyl | α-OTHP | |
| 3,4-dimethoxyphenyl | β-OTHP | |

(a) prepared by the procedure of example 11

Additional prostaglandins of the structure

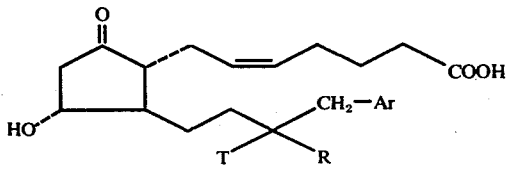

| Ar | T | R | IR data | Isomer (d) |
|---|---|---|---|---|
| phenyl | (a) —OH | —H | 1710 1735 - | M.P. |
| phenyl | (b) —OH | —H | 1710 1735 - | L.P. |
| phenyl | (a) —OH | —CH₃ | 1710 1735 - | (e) |
| -naphthyl | —OH | H | 1710 1735 | M.P. |
| 3,4-dimethoxyphenyl | —OH | H | 1710 1735 | M.P. |

(a) prepared by the procedure of example 16
(d) Mobility on T.L.C. M.P. more polar, L.P. less polar
(e) R.S. mixture separable by high pressure liquid/liquid chromatography Additional compounds of the formula

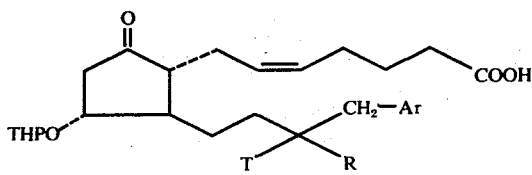

| Ar | T | R | |
|---|---|---|---|
| phenyl | α-OTHP | —H | (a) |
| phenyl | β-OTHP | —H | (a) |
| phenyl | -OH | —CH₃ | (a) |
| β-naphthyl | α-OTHP | H | (a) |
| 3,4-dimethoxyphenyl | β-OTHP | H | (a) |

(a) prepared by the procedure of example 14.
(b) prepared by the procedure of example Additional compounds of the structure

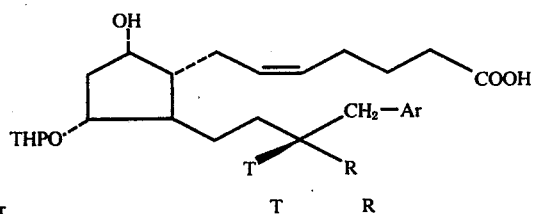

| Ar | T | R | | |
|---|---|---|---|---|
| phenyl | α-OTHP | —H | (a) | 1710 - |
| phenyl | β-OTHP | —H | (a) | 1710 - |
| β-naphthyl | α-OTHP | H | (a) | 1710 - |
| 3,4-dimethoxyphenyl | β-OTHP | H | (a) | 1710 - |

(a) prepared by the procedure of example 12.

Additional prostaglandins of the structure (a)

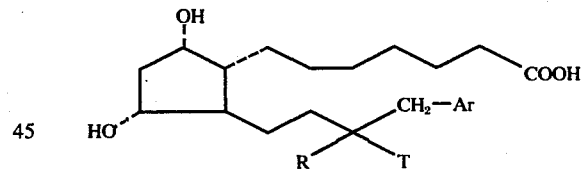

| Ar | T | R | IR data |
|---|---|---|---|
| phenyl | α-OH | H | 1710 |
| phenyl | β-OH | H | 1710 |
| β-naphthyl | α-OH | H | 1705 |
| 3,4-dimethoxyphenyl | α-OH | H | 1707 |

(a) prepared by the procedure of example 13.

Additional prostaglandins of the structure

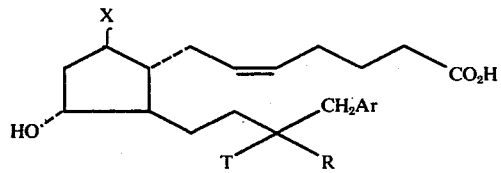

| Ar | T | R | X | Isomer (a) | Isomer (b) |
|---|---|---|---|---|---|
| phenyl | αOH | H | αOH | L.P. | L.P. |
| phenyl | βOH | H | αOH | M.P. | L.P. |
| phenyl | αOH | H | βOH | L.P. | M.P. |
| β-naphthyl | αOH | H | αOH | L.P. | L.P. |

-continued

Additional prostaglandins of the structure

| Ar | T | R | X | Isomer (a) | Isomer (b) |
|---|---|---|---|---|---|
| β-naphthyl | αOH | H | βOH | L.P. | M.P. |
| 3,4-dimethoxyphenyl | αOH | H | αOH | L.P. | L.P. |
| 3,4-dimethoxyphenyl | αOH | H | βOH | L.P. | M.P. |

(a) Mobility on T.L.C. (C-15 epimers) M.P. = more polar, L.P. = less polar.
(b) Mobility on T.L.C. (C-9 epimers) M.P. = more polar, L.P. = less polar.

What is claimed is:

1. 13,14 dihydro-ω-pentanorprostaglandins of the A₂, F₂ and E₂ series having at the 15-position one hydrogen or lower alkyl substituent and one substituent of the formula:

Ar—CH₂— wherein Ar is α- or β-naphthyl; phenyl; 3,4-dimethoxyphenyl; 3,4-methylenedioxyphenyl; 3,4,5-trimethoxyphenyl; or monosubstituted phenyl wherein said substituent is halo, trifluoromethyl, phenyl, lower alkyl or lower alkoxy.

2. A compound of the structure:

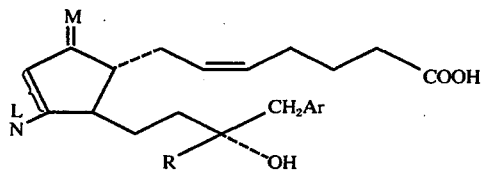

wherein M is = O,

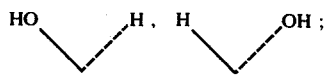

Ar is α- or β-napthyl; phenyl; 3,4-dimethoxyphenyl; 3,4-methylenedioxyphenyl; 3,4,5-trimethoxyphenyl; or monosubstituted phenyl wherein said substituent is halo, trifluoromethyl, phenyl, lower alkyl or lower alkoxy;

R is hydrogen or lower alkyl;

L is a single bond or cis double bond;

N is hydrogen or α-hydroxyl;

and wherein L, M and N are so selected as to complete the structure of a prostaglandin of the A, E or F series.

3. A compound of the structure:

wherein Ar is α- or β-naphthyl; phenyl; 3,4-dimethoxyphenyl; 3,4-methylenedioxyphenyl; 3,4,5-trimethoxyphenyl; or monosubstituted phenyl wherein said substituent is halo, trifluoromethyl, phenyl, lower alkyl or lower alkoxy;

R is hydrogen or lower alkyl.

4. A compound of the structure:

wherein Ar is α- or β-naphthyl; phenyl; 3,4-dimethoxyphenyl; 3,4-methylenedioxyphenyl; 3,4,5-trimethoxyphenyl; or monosubstituted phenyl wherein said substituent is halo, trifluormethyl, phenyl, lower alkyl or lower alkoxy;

and R is hydrogen or lower alkyl.

5. A compound of the structure:

wherein Ar is α- or β-naphthyl; phenyl; 3,4-dimethoxyphenyl; 3,4-methylenedioxyphenyl; 3,4,5-trimethoxyphenyl; or monosubstituted phenyl wherein said substituent is halo, trifluoromethyl, phenyl, lower alkyl or lower alkoxy; and R is hydrogen or lower alkyl.

6. The compound of claim 1 wherein Ar is phenyl, n is 1 and said prostaglandin is 13,14-dihydro PGE₂.

7. The compound of claim 1 wherein Ar is phenyl, n is 1 and said prostaglandin is 13,14-dihydro PGF₂β.

8. The compound of claim 1 wherein Ar is β-naphthyl, n is 1 and said prostaglandin is 13,14-dihydro PGF₂β.

9. The compound of claim 1 wherein Ar is β-naphthyl, n is 1 and said prostaglandin is 13,14-dihydro PGE₂.

10. The compound of claim 1 wherein Ar is phenyl, n is 1 and said prostaglandin is 13,14-dihydro-15-methyl PGE₂.

11. The compound of claim 1 wherein Ar is phenyl, n is 1 and said prostaglandin is 13,14-dihydro PGA₂.

12. The compound of claim 1 wherein Ar is m-tolyl, n is 1 and said prostaglandin is 13,14-dihydro PGE₂.

13. The compound of claim 1 wherein Ar is m-tolyl, n is 1 and said prostaglandin is 13,14-dihydro PGF₂β.

* * * * *